United States Patent [19]

Honma et al.

[11] Patent Number: 4,661,208
[45] Date of Patent: Apr. 28, 1987

[54] METHOD FOR DEHYDRATING DISTILLATION OF AN AQUEOUS SOLUTION OF CARBOXYLIC ACID

[75] Inventors: Yoshihiro Honma, Osaka; Fumiaki Kawamoto, Wakayama; Shozo Tanaka, Osaka, all of Japan

[73] Assignee: Shin-Etsu Vinyl Acetate Co., Ltd., Osaka, Japan

[21] Appl. No.: 747,279

[22] Filed: Jun. 21, 1985

[30] Foreign Application Priority Data

Nov. 2, 1984 [JP] Japan ............................. 59-231677

[51] Int. Cl.⁴ ............................................. B01D 3/36
[52] U.S. Cl. ......................................... 203/15; 203/57; 203/98; 203/99; 203/DIG. 19; 562/608; 159/DIG. 8
[58] Field of Search ................ 203/98, DIG. 19, 99, 203/15, 16, 69, 68, 60, 57; 562/608; 159/DIG. 8

[56] References Cited

U.S. PATENT DOCUMENTS

| | | | |
|---|---|---|---|
| 1,896,100 | 2/1933 | Ricard et al. | 203/15 |
| 1,917,391 | 7/1933 | Othmer | 203/16 |
| 2,050,234 | 8/1936 | Othmer | 203/15 |
| 2,096,734 | 10/1937 | Coator | 203/60 |
| 2,111,140 | 3/1938 | Coutor | 203/60 |
| 2,317,758 | 4/1943 | Guinot | 203/68 |
| 2,485,048 | 10/1949 | Guinot | 203/60 |
| 2,859,154 | 11/1958 | Othmer | 203/69 |
| 3,791,935 | 2/1974 | Eubanks et al. | 203/15 |
| 4,204,915 | 4/1980 | Kurata et al. | 203/69 |
| 4,344,897 | 8/1982 | Goedecke et al. | 203/68 |
| 4,345,976 | 8/1982 | Peter et al. | 203/60 |

FOREIGN PATENT DOCUMENTS 0356787 9/1931 United Kingdom ................ 203/16

Primary Examiner—S. Leon Bashore
Assistant Examiner—V. Manoharan
Attorney, Agent, or Firm—Hopgood, Calimafde, Kalil, Blaustein & Judlowe

[57] ABSTRACT

The invention provides a means for greatly saving the thermal energy consumption in the dehydrating distillation of an aqueous solution of a carboxylic acid such as acetic acid by use of an azeotropically distilling entrainer boiling at a lower temperature than the carboxylic acid and immiscible with water. The improvement proposed by the invention comprises taking at least a part of the entrainer phase separated from the condensate coming from the column top or at least a part of the side-cut fluid abstracted from the refluxing fluid inside the column, evaporating the thus taken fluid into vapor and introducing the vapor into the distillation column at a stage for the introduction of the starting feed or below.

1 Claim, 7 Drawing Figures

METHOD FOR DEHYDRATING DISTILLATION OF AN AQUEOUS SOLUTION OF CARBOXYLIC ACID

BACKGROUND OF THE INVENTION

The present invention relates to a method for the dehydrating distillation of an aqueous solution of a carboxylic acid such as acetic acid with high thermal efficiency.

Several methods are known in the prior art for the separation of water from an aqueous solution of a carboxylic acid such as acetic acid by distillation including a method in which dehydration is performed by the extraction of acetic acid with an organic solvent followed by azeotropic distillation of the solvent and water and a method in which dehydration is performed by the direct azeotropic distillation of an aqueous solution of the carboxylic acid with admixture of an organic solvent to remove the solvent and water with omission of the procedure of extraction.

Although less disadvantageous in respect of the thermal energy consumption than other methods using no organic solvent, the above mentioned methods still have a problem of the costs for a large quantity of thermal energy required to remove the organic solvent and water in the dehydrating azeotropic distillation.

SUMMARY OF THE INVENTION

An object of the present invention is therefore to provide a novel and very efficient method for the dehydrating distillation of an aqueous solution of a carboxylic acid such as acetic acid in which consumption of thermal energy can be greatly reduced in comparison with conventional methods.

Thus, the present invention provides an improvement which comprises, in the dehydrating distillation of an aqueous solution of a carboxylic acid by use of an entrainer having a boiling point lower than that of the carboxylic acid and immiscible with water, taking at least a part of the entrainer phase out of the fluid condensate of the vapor withdrawn from the column top or withdrawing at least a part of the side-cut out of the refluxing fluid inside the distillation column, evaporating the fluid thus taken out or withdrawn into a vapor, and feeding the vapor to the dehydrating distillation column at a stage in the column which is at or below the stage in the column at which the starting material is fed into the column for feeding of the starting material.

DETAILED DESCRIPTION OF THE PREFERRED EMBODIMENTS

The above described method of the present invention is applicable to the dehydrating distillation of an aqueous solution of a carboxylic acid distillable and miscible with water such as formic acid, acetic acid, propionic acid and the like. The entrainer here implied is an organic liquid compound which is not freely miscible with water in the vapor condensate at the column top. Suitable entrainers include, though not limitative thereto, aromatic hydrocarbon compounds such as benzene and toluene, aliphatic hydrocarbon compounds such as hexane and ester compounds such as ethyl acetate. If desired, a combination of two kinds or more of these organic solvents can be used.

In the following, the method of the present invention is described in detail with reference to the accompanying drawing.

Figure 1A:
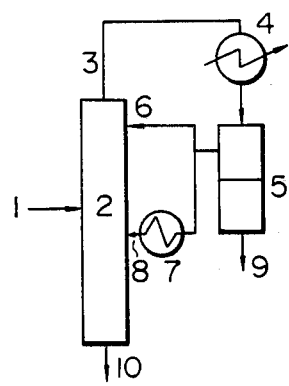
FIGS. 1a to 1e each schematically illustrate the flow diagram in the apparatus used in the inventive method.

In the flow diagram illustrated in FIG. 1a, the aqueous solution of a carboxylic acid is, through the piping 1, introduced into the distillation column 2 at an intermediate height. The water contained in the thus introduced aqueous solution forms an azeotropic mixture with the entrainer ascending in the column and the vapor thereof at the column top 3 is introduced into the condenser 4 where it is condensed into a condensate. The condensate is introduced into the decanter 5 and separated into an aqueous phase and an entrainer phase. The aqueous phase is discharged out of the decanter 5 through the outlet piping 9 and discarded. A part of the entrainer phase in the decanter 5 is returned to the column top through the piping 6 while the remainder thereof is introduced into the column 2 at an intermediate height through the piping 8 after evaporation in the heat exchanger 7. It is optional that the whole volume of the entrainer phase in the decanter 5 is vaporized in the heat exchanger 7 to be introduced into the column 2 in the form of a vapor provided that the volume of the refluxing fluid in the column 2 is sufficiently large by means of an in-column partial condenser (not shown in the figure) or the like. The carboxylic acid thus dehydrated by distillation is discharged at the column bottom through the piping 10.

Figure 1B:
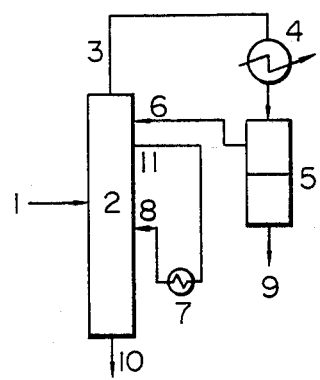

In FIG. 1b illustrating another flow diagram according to the inventive method, a part of the refluxing fluid in the distillation column 2 is taken out as a side-cut through the piping 11 and recycled to the column 2 at a stage for starting feed or below in the form of a vapor after evaporation in the heat exchanger 7. It is optional that the side-cut fluid taken out is partly or wholly evaporated.

In the method of the present invention, the heat supply required for the vaporization of the entrainer is obtained by efficiently utilizing the vapor at the column top and the discharge out of the still at the column bottom so that a great saving can be achieved in the consumption of the thermal energy.

Figure 1C:
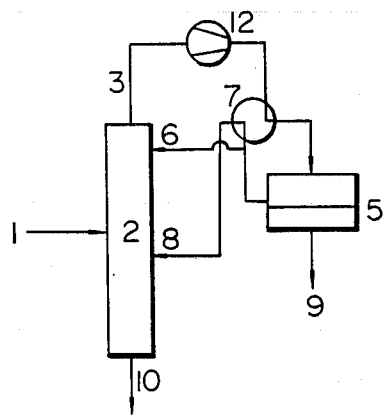

In the flow diagram illustrated in FIG. 1c, the vapor coming cut of the column top 3 is compressed in the compressor 12 and then introduced into a heat exchanger, 7, where the vapor is liquified. This liquid is introduced into the decanter 5. A part of the entrainer phase separated in the decanter is removed from the decanter and introduced into the heat exchanger. The entrainer heated and vaporized in the heat exchanger 7 is introduced into the column 2 through the piping 8 while the remainder of the entrainer phase in the decanter 5 is introduced into the column 2 through the piping 6 in the liquid form as such.

Figure 1D:
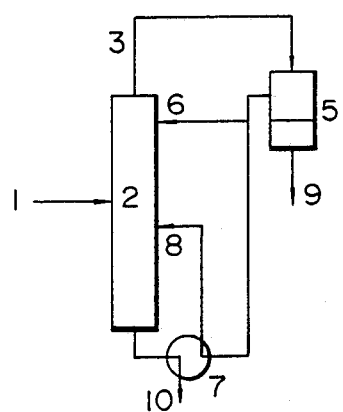

In the flow diagram illustrated in FIG. 1d, the entrainer phase obtained in the decanter 5 is partly introduced into the column 2 through the piping 6 in the liquid form as such while the remainder thereof is vaporized by being heated in the heat exchanger 7 with the discharge out of the column bottom and introduced into the column through the piping 8 in the form of a vapor.

Figure 1E:
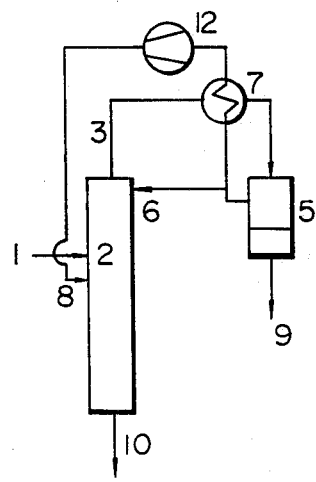

In the flow diagram illustrated in FIG. 1e, the entrainer phase obtained in the decanter 5 is partly introduced into the column 2 through the piping 6 in the liquid form as such while the remainder thereof is vaporized by the heat exchange in the heat exchanger 7 with the vapor coming out of the column top 3 and, after compression in the compressor 12, is introduced in the liquid form into the column 2 at a stage for the starting feed or below through the piping 8.

The above described flow diagrams illustrated in the figures are only several of the possible embodiments of the inventive method including modifications in which the temperature of the fluid is increased by means of a compression heat pump, absorption heat pump or chemical heat pump when the fluid is at an insufficient temperature as a heat exchange medium with the entrainer, the entrainer liquid subjected to the heat exchange is brought under reduced pressure to accelerate evaporation or combination of these means.

The azeotropic distillation in the inventive method for the dehydration of an aqueous solution of a carboxylic acid can be performed with a heat source which is not at high temperatures but only sufficient to vaporize the entrainer because the temperature difference between the top and bottom of the distillation column is not so large as in the conventional methods of direct vapor compression. For example, the temperature of the heat source for the evaporation of the entrainer can be as low as 100° C. when the entrainer is ethyl acetate boiling at 74° C.

Accordingly, an advantage of the inventive method is in the utilization of a low-temperature heat source with which an aqueous solution of a carboxylic acid can be subjected to dehydrating distillation in a very high efficiency.

In the following, the method of the invention is described in more detail by way of examples and comparative examples.

EXAMPLES 1 TO 3 AND COMPARATIVE EXAMPLE 1

Figure 2:
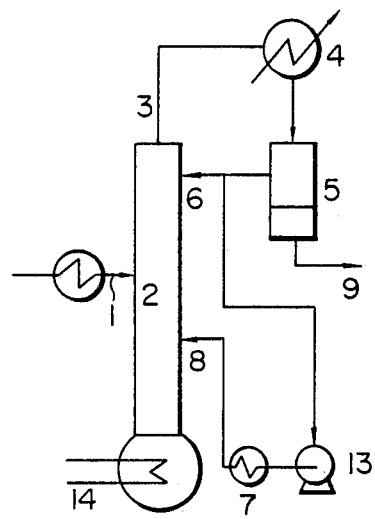
FIGS. 2 and 3 each schematically illustrate a different flow diagram in the inventive method.

A 50% by weight aqueous solution of acetic acid was subjected to dehydrating distillation according to the flow diagram illustrated in FIG. 2. The glass-made distillation column 2 having an inner diameter of 3 cm contained packings (Helipack No. 3) up to a height of 120 cm and the entrainer was a 50:50 by weight mixture of benzene and ethyl acetate. The acetic acid solution preheated in an oil bath (not shown in the figure) was introduced at a constant feed rate of 392 g/hour into the column 2 at an intermediate height 45 cm below the column top 3 through the piping 1. The thermal energy for conducting the distillation was supplied at a constant rate of 113 kilocalories/hour from the reboiler 14 connected to the column bottom. The distillate coming out of the column top 3 was cooled and condensed in the condenser 4 and the condensate was introduced into the decanter 5 where it was separated into the aqueous phase and the entrainer phase. A part of the entrainer phase discharged out of the decanter 5 was introduced by means of a metering pump 13 into an oil bath 7 to be completely vaporized therein and the vapor was introduced into the column 2 throught the port 8 at a height 25 cm below the stage for the starting feed while the remainder of the entrainer phase was returned to the column top through the piping 6 in the lipuid form as such. The aqueous phase in the decanter was discharged at the bottom thereof through the piping 9. In a comparative test, whole volume of the entrainer phase obtained in the decanter 5 was returned as such to the column top by omitting the external circuit to the intermediate height of the column 2 through the metering pump 13 and the oil bath 7.

Table 1 below summarizes the rate of water separation in g/hour when the flow rate of the entrainer through the external circuit was varied from zero (Comparative Example 1) to 2000 g/hour (Example 3).

As is understood from the results shown in Table 1, the increase of the flow rate of the entrainer through the external circuit had a great effect of increasing the rate of water separation.

EXAMPLES 4 AND 5 AND COMPARATIVE EXAMPLE 2

Figure 3:
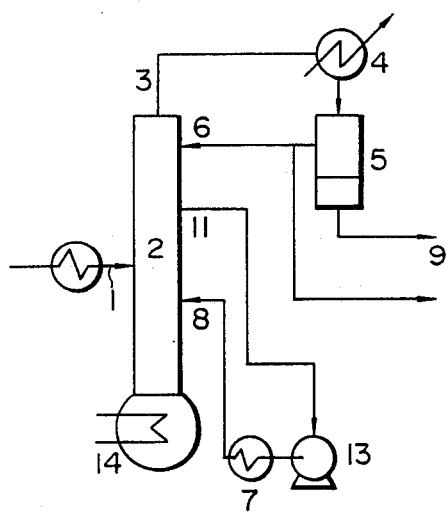

According to the flow diagram illustrated in FIG. 3, a liquid mixture composed of 76% by weight of acetic acid, 16% by weight of vinyl acetate and 8% by weight of water was introduced at a constant rate of 1269 g/hour into the same distillation column 2 as used in the preceding examples at a height 50 cm below the column top. In this case, the role of the entrainer was played by the vinyl acetate contained in the starting feed. The side-cut port 11 provided to the column 2 at a height 20 cm below the column top served to abstract a part of the fluid refluxing in the column 2 by means of a metering pump 13 and the thus abstracted fluid was completely vaporized in an oil bath 7 to be introduced into the column 2 through the port 8 at a height 20 cm below the stage for the starting feed in the form of a vapor. The side-cut fluid abstracted from the side-cut port 11 was a uniform solution composed of 99.0% by weight of vinyl acetate, 0.9% by weight of water and a trace amount of acetic acid. The rate of heat supply to the reboiler 14 at the column bottom was constant at 152 kilocalories/hour. In Comparative Example 2, the external circuit for the circulation of the entrainer was omitted.

Table 1 also gives the flow rate of the entrainer circulating through the external circuit and the results of the rate of water separation in these experiments.

EXAMPLE 6

The experimental conditions were substantially the same as in Examples 4 and 5 except that the external circuit through the side-cut port 11, metering pump 13 and oil bath 7 was omitted and, instead, the condensate obtained at the column top 3 was separated into the organic and aqueous phases and a part of the organic phase was completely evaporated in an oil bath to be introduced into the column 2 at a height 20 cm below the stage for the starting feed. The organic phase separated from the condensate at the column top contained 1.8% by weight of water and trace amounts of other low-boiling compounds, the balance being vinyl acetate. The rate of water separation is shown in Table 1 together with the flow rate of the entrainer circulating through the external circuit.

In each of Examples 4 to 6, the acetic acid discharged out of the column bottom contained no detectable amount of the entrainer and no acetic acid could be detected in the aqueous phase obtained in the decanter 5 by separating the condensate coming from the column top 3.

TABLE 1

| | Flow rate of entrainer through external circuit, g/hour | Rate of water separation, g/hour |
|---|---|---|
| Comparative Example 1 | — | 51.1 |
| Example 1 | 500 | 90.7 |
| Example 2 | 1000 | 128.8 |
| Example 3 | 2000 | 194.6 |
| Comparative Example 2 | — | 33.1 |
| Example 4 | 1000 | 65.4 |
| Example 5 | 1500 | 79.0 |
| Example 6 | 1000 | 57.2 |

What is claimed is:

1. A method for dehydrating an aqueous solution of a carboxylic acid by distillation in the presence of a water immiscible entrainer which has a lower boiling point than the boiling point of the carboxylic acid and which forms an azeotropic mixture with water, comprising, (a) introducing an aqueous solution of a carboxylic acid into a distillation column at a stage in the column positioned at an intermediate height wherein the water contained in the aqueous solution forms an azeotropic mixture with the entrainer ascending the column;

(b) removing a side-cut portion of a refluxing fluid from a stage in the column above the stage of the introduction of the aqueous solution and below the top of the column;

(c) introducing the side-cut portion into a heat exchanger;

(d) vaporizing the side-cut portion;

(e) introducing the side-cut portion vapor into the column at a stage in the column below the stage of introduction of the aqueous solution;

(f) removing the vapors of the azeotropic mixture from the top of the distillation column and introducing the vapors into a condenser;

(g) condensing the vapors into condensate;

(h) removing the condensate from the condenser and introducing it into a decanter;

(i) separating the condensate in the decanter into an aqueous phase and entrainer phase;

(j) discarding the aqueous phase;

(k) returning and introducing the entrainer phase into the top of the distillation column; and (l) discharging the dehydrated carboxylic acid from the bottom of the distillation column.

* * * * *